United States Patent
Haag et al.

(10) Patent No.: US 9,090,495 B2
(45) Date of Patent: Jul. 28, 2015

(54) SLOW RELEASE TABLET COMPOSITION FOR TREATING INDUSTRIAL WATER SYSTEMS

(75) Inventors: Anthony P Haag, Bozeman, MT (US); Attila G Relenyi, Midland, MI (US)

(73) Assignee: AMSA, Inc., Midland, MI (US)

( * ) Notice: Subject to any disclaimer, the term of this patent is extended or adjusted under 35 U.S.C. 154(b) by 1094 days.

(21) Appl. No.: 12/994,742

(22) PCT Filed: Mar. 12, 2010

(86) PCT No.: PCT/US2010/000766
§ 371 (c)(1),
(2), (4) Date: Nov. 24, 2010

(87) PCT Pub. No.: WO2010/117406
PCT Pub. Date: Oct. 14, 2010

(65) Prior Publication Data
US 2011/0073802 A1    Mar. 31, 2011

Related U.S. Application Data

(60) Provisional application No. 61/212,009, filed on Apr. 6, 2009.

(51) Int. Cl.
| | |
|---|---|
| C02F 5/12 | (2006.01) |
| C09D 5/16 | (2006.01) |
| C02F 1/68 | (2006.01) |
| A01N 33/08 | (2006.01) |
| C02F 1/50 | (2006.01) |
| C02F 5/10 | (2006.01) |
| C02F 103/02 | (2006.01) |

(52) U.S. Cl.
CPC ............... *C02F 1/688* (2013.01); *A01N 33/08* (2013.01); *C02F 1/50* (2013.01); *C02F 5/10* (2013.01); *C02F 2103/023* (2013.01); *C02F 2303/08* (2013.01); *C02F 2303/12* (2013.01)

(58) Field of Classification Search
None
See application file for complete search history.

(56) References Cited

U.S. PATENT DOCUMENTS

| | | |
|---|---|---|
| 4,800,082 A | 1/1989 | Karbowski et al. |
| 4,816,061 A | 3/1989 | Walter, Jr. et al. |
| 5,155,131 A | 10/1992 | Relenyi et al. |

(Continued)

OTHER PUBLICATIONS

D. R. Kelly, D. A. Little, & D. J. Dobrez, NACE International Corrosion Conference, Paper No. 07069, "An Alternative Method for Delivering Cooling Water Treatment Chemicals Using Controlled Release Technology", in 2007.

(Continued)

*Primary Examiner* — Joseph D Anthony
(74) *Attorney, Agent, or Firm* — Technology Law PLLC; Karen L. Kimble

(57) ABSTRACT

The present invention provides for a slow release composition, preferably as a tablet, for industrial water systems, under an alkaline pH or high water hardness, using as an active ingredient a multifunctional amine of Formula (I) and a hydrophilic polymer, and other components such as a compression agent, in one composition as a biocide, biostat, biodispersant, deposit penetrant aid, organic deposit remover, detergent, surfactant, antifoam, scale inhibitor, scale remover, and a corrosion inhibitor. The composition is used in multiple water cycles, can remove, disperse or inhibit fouling. The active ingredient(s) of the composition is released over a long time, up to 6 months.

21 Claims, 6 Drawing Sheets
(2 of 6 Drawing Sheet(s) Filed in Color)

(56) References Cited

U.S. PATENT DOCUMENTS

| | | | |
|---|---|---|---|
| 5,514,287 A | 5/1996 | Jones et al. | |
| 5,603,941 A | 2/1997 | Farina et al. | |
| 5,684,048 A | 11/1997 | Ajoku et al. | |
| 5,720,950 A * | 2/1998 | Poiani et al. | 424/78.29 |
| 6,607,694 B1 | 8/2003 | Blakemore et al. | |
| 6,863,830 B1 | 3/2005 | Purdy et al. | |
| 7,824,557 B2 * | 11/2010 | Whitekettle et al. | 210/755 |
| 2003/0228373 A1 | 12/2003 | Ludensky et al. | |
| 2006/0165745 A1 | 7/2006 | Chew et al. | |
| 2007/0251889 A1 | 11/2007 | Singleton et al. | |
| 2009/0039035 A1 * | 2/2009 | Whitekettle et al. | 210/764 |
| 2011/0052656 A1 * | 3/2011 | Whitekettle et al. | 424/421 |
| 2012/0080641 A1 * | 4/2012 | Relenyi | 252/180 |

OTHER PUBLICATIONS

SM Bilek, NT Greene, BE Moriarty and RS Walicki, International Water Conference, Paper IWC-08-40, "Solid Chemical Programs for Scale and Corrosion Control in Cooling Water Systems: Delivering Sustainable Development", held Oct. 28, 2008.

\* cited by examiner

US 9,090,495 B2

SLOW RELEASE TABLET COMPOSITION FOR TREATING INDUSTRIAL WATER SYSTEMS

CROSS REFERENCE TO RELATED APPLICATIONS

This application claims priority from all the following listed applications and is a national phase application from International Application PCT/US2010/000766, filed 12 Mar. 2010, which claims priority from U.S. Application 61/212,009, filed 6 Apr. 2009.

FIELD OF THE INVENTION

The present invention provides a composition for the treatment of industrial water systems using multifunctional ingredients as a biofilm dispersant, scale inhibitor, biocide, and corrosion inhibitor, which provide sustained release or controlled release of the ingredients.

BACKGROUND OF THE INVENTION

The ability to control the various fouling issues for industrial water systems has long been sought. Fouling refers to biofilm including its formation, organic deposits including their formation, metal corrosion, surface discoloration or any other adverse consequences in industrial systems that are directly, indirectly or otherwise due to the presence or action of microorganisms that are freely floating in a liquid or are associated with a surface of such industrial water system or inorganic deposits including their formation due to the concentration and precipitation of compounds present in hard water of such industrial water system. Organic deposits include non-viable microbial cells and their associated organic products, such as cellular proteins, lipids, and nucleic acids. In particular, organic deposits include polysaccharides. Compounds which disperse such organic deposits are referred to as biodispersants. To control such fouling refers to prevention, reduction or removal of such fouling.

Various methods to have a slow release formulation for water systems have been attempted that would provide: 1) continuous applications to an industrial water system by non-mechanical means (i.e., without the use of pumps, an eductor or dispersing apparatus); 2) relatively constant concentrations of the active compound in spite of the water turnover in the industrial water system over a long time; and 3) ease of treatment relative to manual introduction of liquids to minimize environmental and personnel exposure issues.

To provide those objectives, slow release tablets of various types have been tried. For example, a tablet using 2,2-dibromo-3-nitrilopropionamide (DBNPA) as an active ingredient biocide, hydrophilic polymer and compression agent has been made (see U.S. Pat. No. 4,800,082). However, there are no other actives in this formulation. Because there are no biodispersants, scale inhibitors or corrosion inhibitors used, those would need to be added separately as required for the specific water conditions. The active ingredient DBNPA, at alkaline pH, such as pH~9 in industrial water system conditions, is degraded under these end use conditions in a few minutes.

U.S. Pat. No. 4,816,061 discloses a method for biocide use at an alkaline pH (7.5-12) or high water hardness using an n-decylthioethylamine as the active ingredient. There is no solid formulation or slow release method disclosed. There is no presence of other actives in one formulation mentioned. A typical dose of this patented composition is effective for 1-1.5 days in a typical cooling tower system. The active ingredient does not react with other typical water treatment ingredients which may be added.

In recirculating water systems U.S. Pat. No. 5,514,287 discloses a tablet composition containing a boron source material, a halogen source material, and glycoluril. The tablet is used in conjunction with a boron source material and a periodic addition of a chlorine source material, which are added directly to the water. This is a tablet formulation having only active ingredients that are quick dissolving and therefore is used to avoid the addition of liquid chemicals. There is no hydrophilic polymer present to control the release rate of the active ingredients. There are no scale inhibitors or corrosion inhibitors used so those would need to be added as required for the specific water conditions. The use of these patented tablets is for swimming pools. Such pH conditions for swimming pools are usually ~7, while pH conditions for industrial water systems are more alkaline, such as pH 8 and above.

A multilayer tablet was made in U.S. Pat. No. 6,863,830 where there was a fast dissolving layer and a slow dissolving layer. Hydrophilic polymers are taught as binders but not used as control release agents. The examples show that the rate of dissolution is a property of the individual chemicals used or their mixtures; it is not based on any polymer matrix. Two layers are required to obtain the results. There is no discussion of alkaline pH conditions in the water systems they tested.

When a vehicle cooling system is the water source, a controlled release system was used in U.S. Pat. No. 6,607,694. It contains a core of active ingredients which may contain a hydrophilic polymer as a binder, and an insoluble coating that controls the rate of release. There is no biocide or organic deposit control actives that are needed for industrial water systems present.

At a NACE International Corrosion Conference in 2007, Paper No. 07069 disclosed using controlled release technology for cooling towers. Various diffusion methods were discussed but these tablets required a core of active (such as corrosion inhibitor and scale inhibitor) and a polymer coating which controlled the release rate for about 30 days. There was no biocide or organic deposit control agent present in the tablet, but it was added separately.

U.S. Pat. No. 5,603,941 describes a solid tablet comprising a biocide and biodispersant for industrial, household, and recreational water applications. The rate of dissolution is not described, but presumably is determined by the solubility of its chemical components. It does not have a hydrophilic polymer matrix to effect slow release, and there is no specification of the water that is to be treated, such as pH or hardness.

At the International Water Conference held on Oct. 28, 2008, paper number IWC-08-40 disclosed the use of a solid mixture of scale and corrosion inhibitors in the form of a tablet containing 100% active ingredient and thus had no hydrophilic polymer. The tablets are dissolved in water in a separate vessel and then the resultant solution is fed into the water system with automated pumps as needed. The active ingredients are not slowly released. Different formulations were used for hard and soft water applications.

U.S. Published Application 2006/0165745 discloses a tablet for sustained release in water systems. The tablet has a hydrophilic polymer and an active ingredient and requires a curing step to a specified water level by steaming the tablets or by setting them out at room temperature in humidity. This curing step that requires addition of water is stated to be important so that the tablet does not prematurely disintegrate during use. The release of the active ingredient occurs over 30 days. There is no discussion of the pH being alkaline in the water system or water hardness as found in industrial water systems.

Currently sold are solid forms of biocides with binders. These solids are then put into a closed chamber and water is introduced at a sufficient high pressure to erode the solid into smaller pieces or to dissolve it. Without this ablative action of the water these solids cannot be dissolved into the water system.

Clearly, it would be desirable to have several actives or one multifunctional active in one solid form, such as a tablet composition, which provides a sustained release over a long time, where multiple water cycles in a water circulation system are possible, under alkaline pH or high water hardness, and be effective against fouling in industrial water systems. Additionally, there are no such slow release compositions presently known that are effective to remove, to inhibit, and to control fouling in industrial water systems.

BRIEF SUMMARY OF THE INVENTION

The present invention provides a composition for the treatment of industrial water systems, under an alkaline pH or high water hardness, using a multifunctional ingredient of Formula (I) as defined below, a hydrophilic polymer and other ingredients, such as a compression agent, in one composition as a biocide, biostat, biodispersant, deposit penetrant aid, organic deposit remover, detergent, surfactant, scale inhibitor, scale remover and corrosion inhibitor, which provide sustained release or continuous release of the ingredients over time. In one aspect, the components of the present composition display enhanced properties compared to their individual properties alone. All these components may be present in one composition when all the properties are desired or only the required components when fewer properties are desired, such as the conditions found in a specific industrial water system. In another aspect, multiple water cycles in a water circulation system are possible while maintaining activity while using the composition of this invention.

This composition of the present invention provides a slow release composition for industrial water systems which comprises:

a) from about 1 through about 95% by weight of a compound of Formula (I)

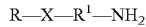

wherein:
R is a straight chain or branched chain $C_6$-$C_{18}$ alkyl or a straight chain or branched chain $C_6$-$C_{18}$ alkoxy-$C_2$-$C_3$-alkyl, preferably a straight chain or branched chain $C_6$-$C_{18}$ alkyl, more preferably a straight chain or branched chain $C_8$-$C_{14}$ alkyl;
$R^1$ is a straight chain or branched chain $C_2$-$C_4$ alkyl; and
X is S, O or N—$R^2$ wherein $R^2$ is H or a straight chain or branched chain $C_1$-$C_8$ alkyl, preferably $R^2$ is H, more preferably S or O; or
the organic or inorganic acid addition salts thereof; and
b) from about 5 through about 99% by weight of a hydrophilic polymer or mixtures of them; and
c) from 0 through about 70% by weight of a compression agent; and
d) from 0 through about 50% by weight of a scale inhibitor; and
e) from 0 through about 20% by weight of a corrosion inhibitor; and provided that one or more of the following occur:

i) it is used in multiple water cycles in a water circulation system while maintaining activity; or
ii) it removes, disperses, or inhibits biofilm deposits; or
iii) it removes, disperses, or inhibits organic deposits; or
iv) the slow release of the active components of the composition in such industrial water system is complete in from about 1 day to about 6 months, preferably from about 1 to about 16 weeks.

The compounds of Formula (I) can serve as a multifunctional ingredient in this composition for removing or dispersing organic deposits, for removing or dispersing biofilm deposits, and/or for removing or dispersing polysaccharide deposits. In addition these compounds facilitate penetration of biocides into the surface bound deposits. A key benefit of this removal, dispersion, and elimination of such depositions is the reduction of the amount of biocide necessary to achieve biocidal kill or to maintain biostatis. Furthermore, these compounds of Formula (I) reduce the amount of corrosion inhibitor and inorganic scale inhibitors required. These compounds of Formula (I) also function as a broad spectrum biocide, an ore floatation agent, and a corrosion inhibitor. It was unexpected to find a slow release composition of this invention that will work under one or all of these conditions for a long time and control fouling, including inorganic, organic, microbial and corrosion. Other components can be added to this composition when desired, such as anti-foaming agents [e.g., Dow Corning™ Antifoam H-10 Emulsion, Dow Corning™ 2-42485, Dow Corning™ 1920, Tergitol™ L-62 (The Dow Chemical Company), Hi-Mar DFC-455 (Hi-Mar Specialty Chemicals LLC), Hi-Mar DFC-21, Hi-Mar N-206 HS] from about 0.5 to about 10% by wt or mold release agents (e.g., calcium stearate, stearic acid, polyethyleneglycol, and silicones) from about 0.5 to about 10% by wt.

In one other aspect these compositions are for the treatment of industrial water systems that operate at an alkaline pH (pH=about 7.1 to about 12) or high water hardness (from about 70 ppm to about 2,000 ppm). General hardness is a measure of the concentration of $Ca^{2+}$ and $Mg^{2+}$ per volume of water. For example, paper test strips measure hardness in ppm, where 1 ppm=1 mg of $CaCO_3$ per liter of water.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Glossary

Figure 1:
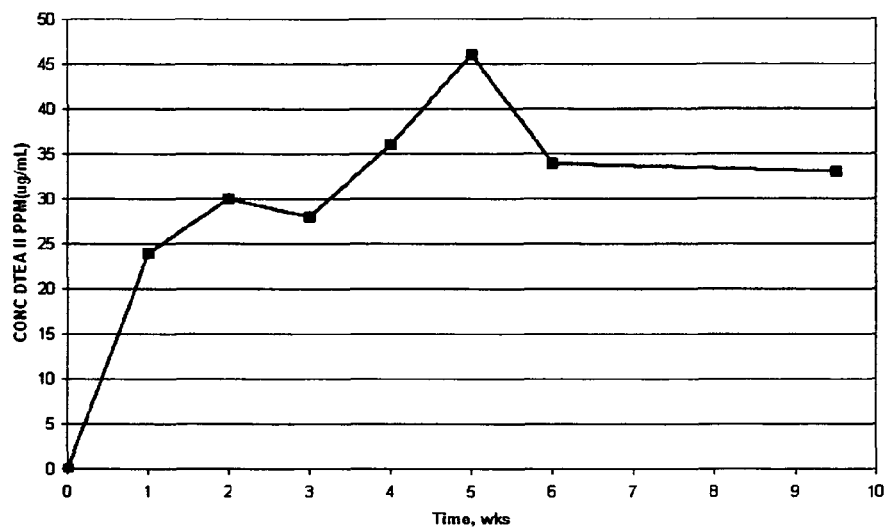
FIG. 1 shows DTEA II® concentration vs. time for Example 2, Sample 1 and its slow release over 9.5 weeks.

The following terms as used in this application are to be defined as stated below and for these terms, the singular includes the plural.

about means±3% by weight absolute when used with any numerical value but does not exceed 100 or less than zero biodispersant(s) means compounds which disperse organic deposits cfu means colony forming unit cm means centimeters CMC means carboxymethylcellulose DCP means dicalcium phosphate ($CaHPO_4$)

fouling means biofilm (including its formation), organic deposits (including their formation), metal corrosion, surface discoloration or any other adverse consequences in industrial systems that are directly, indirectly or otherwise due to the presence or action of microorganisms that are freely floating in a liquid or are associated with a surface of such industrial water system or inorganic deposits including their formation due to the concentration and precipitation of compounds present in hard water of such industrial water system g means grams gal means gallons Guar means galactomannan h means hours HEC means hydroxyethylcellulose HEDP means 1-hydroxyethylidene-1,1-diphosphonate HP means hydrophilic polymer, such as a water-swellable polymer HPC means hydroxypropylcellulose HPMC means hydroxypropyl methylcellulose L means liters; 1 L=0.26 gal m means meters MC means methylcellulose MCC means microcrystalline cellulose mil means one thousandth of an inch (0.0254 millimeter)

min means minutes mL means milliliters mPa·s means millipascals times seconds; equivalent to 1 centipoise mpy means mils per year Organic deposits means non-viable microbial cells and their associated organic products, such as cellular proteins, lipids, nucleic acids, and polysaccharides.

PEG means polyethylene glycol ppm means parts per million

PVP means polyvinylpyrrolidone

RT means refrigeration tons

µS/cm means microsiemens per centimeter (conductivity unit)

slow release means that the active ingredients in the present composition are fully released into the water system over from about 1 day to about 6 months, preferably from about 1 to about 16 weeks, and more preferably from about 1 to about 4 weeks tablet means the present composition in the form of a solid or semisolid tablet or other form that allows it to be placed below the water line of the container in an industrial water system yr means year % by wt means percent by weight Industrial water systems includes cooling towers, metal working fluids, pulp and paper systems, air washers, air scrubbers, produced water in oil production, enhanced oil recovery systems, oil field flooding systems, gas transmission line systems, hydrotesting water systems, fire water storage systems, high purity water storage systems, printing press water storage systems, semiconductor manufacturing water systems, air handling systems, swamp coolers, water drains and piping systems, drip pans, water condensate piping, comfort cooling tower systems, nuclear primary and secondary water cooling systems, reverse osmosis systems, ultrafiltration water systems, microfiltration water systems, pulp storage systems, and sump collection water systems, and similar systems. These are commercial systems for the treatment of water. As described in the background of this specification, fouling is a significant concern in these systems.

The present invention provides a composition that is especially beneficial for treatment of industrial water systems as it provides multifunctional uses in one composition that dissolves slowly over time. Particularly, the present composition provides a multifunctional active ingredient in the compounds of Formula (I), which multifunctional characteristics are not available in other actives, and also may have other actives present in the composition. The composition can be in the form of a solid or semisolid tablet or other form that allows it to be placed below the water line of the container in an industrial water system, e.g., in a mesh bag or a dispensing device to place on the wall of the industrial container below the water line or where it is exposed to the water. All of these forms are referred to in this invention as "tablets".

The present industrial water systems have water treated that has an alkaline pH or has a high water hardness component or both. These two conditions, pH and hardness, can be connected in the particular system or need not be. For example, the mineral content such as calcium combines with carbonates that are present and forms scale (fouling). This scale is often observed at the waterline. Over time this scale traps dust and dirt and provides a hosting site for microbiological growth which discolors, turns black and the water gets cloudy or murky and looses sparkle. The carbonate deposit can plate out on filters or heat transfer surfaces thereby causing loss of effectiveness. Corrosion is a serious issue that is caused by deposits referred to as "under deposit corrosion". When pH rises, the usual additive of a chlorine biocide or a source of chlorine biocide ceases to be effective, for example when the pH rises to 8, only about 20% of the chlorine is useful and the rest is not available or is lost by conversion to other products such that the amount needed to be added rises significantly to provide the desired benefit.

Water hardness is the precise measure of the mixture of minerals dissolved in the water and is affected by the water's pH and temperature. That mixture of conditions determines the behavior of the hardness. The effects of high water hardness therefore vary in different water systems around the world, but the high water hardness range for this invention is from 70 ppm to ≥2,000 ppm. Unexpectedly, the present composition can be effective in this entire range of high water hardness.

The alkaline pH that is found in many industrial water systems is from pH about 7.1 to about 12. Unexpectedly, the present composition can be effective in this entire range of alkaline pH. Surprisingly, it was found that as the pH is increased, the performance or efficacy is more efficient. These characteristics for the present composition, i.e., to be effective over a wide range of alkaline pH, and to be effective in high water hardness, have not been known previously for a slow release, single tablet. Furthermore, the present composition can be used effectively under all these conditions.

Additionally, these compositions are able to be used in industrial water systems, such as cooling towers wherein the water is circulated and evaporation occurs and water is replaced. Multiple water cycles are performed in these systems but without addition of more composition of this invention. During operation with multiple water cycles, the concentration of dissolved minerals increases. The composition of this invention effectively prevents fouling under these conditions. Such multiple water cycles are from 1 to about 9 cycles, preferably from about 2 to about 5 cycles. This feature of the present composition is important as maximizing cooling tower cycles before further treatment offers many benefits, such as reducing water consumption, minimizing waste generation, decreasing chemical treatment requirements, and lowering overall operating costs. Potential cost saving vary from plant to plant, depending on the cost for raw water, waste disposal costs, chemical treatment dosages and energy costs. Only the present slow release, single composition is able to allow such water reuse cycles while maintaining effectiveness for the abatement of fouling.

Additionally, the release time of the present composition is a slow release in the range of about 1 day to about 6 months, preferably from about 1 to about 16 weeks, more preferably from about 1 to about 4 weeks, before another treatment is required. The various components of the composition are varied depending on the desired form of the composition and end properties desired for the particular conditions of the industrial water system.

One required component of the composition is DTEA II® (trademark, Antimicrobial Specialists & Associates, Inc.) that has the formula

$$R\text{—}X\text{—}R^1\text{—}NH_2 \qquad (I)$$

wherein:

R is a straight chain or branched chain $C_6$-$C_{18}$ alkyl or a straight chain or branched chain $C_6$-$C_{18}$ alkyloxy-$C_2$-$C_3$-alkyl;

$R^1$ is an straight chain or branched chain $C_2$-$C_4$ alkyl; and

X is S, O or N—$R^2$ wherein $R^2$ is H or a straight chain or branched chain $C_1$-$C_8$ alkyl; or the organic or inorganic acid addition salts thereof.

Preferred compounds of Formula (I) are where R is a straight chain or branched chain $C_6$-$C_{18}$ alkyl, preferably a $C_8$-$C_{14}$ alkyl; and X is S, O, or N—$R^2$ wherein $R^2$ is H, preferably where X is S or O. These compounds of Formula (I) are a multifunctional ingredient in this composition for removing or dispersing organic deposits, for removing or dispersing biofilm deposits, and/or for removing or dispersing polysaccharide deposits. In addition these compounds facilitate penetration of biocides into the surface bound deposits. A key benefit of this removal, dispersion, and elimination of such depositions is the reduction of the amount of biocide necessary to achieve biocidal kill or to maintain biostatis. Furthermore, these compounds of Formula (I) reduce the amount of corrosion inhibitor and inorganic scale inhibitors required. These compounds of Formula (I) also function as a broad spectrum biocide, an ore floatation agent, and a corrosion inhibitor. This functionality is very different from other previously known actives that have been tried for this purpose as they have displayed only one function. Thus lower amounts of active components are required to attain the desired fouling control results. Also these compounds of Formula (I) are active under an alkaline pH or high water hardness, including the present composition. Most other known actives cannot function in such conditions.

The Formula (I) compounds are a liquid, usually as a water-free concentrate or as an aqueous solution from 1-100% by weight of solution. Preferred embodiments of Formula (I) are n-decylthioethylamine, n-decylaminoethylamine, octyloxypropyl-1,3-diaminopropane, isodecyloxypropyl-1,3-diaminopropane, isododecyloxypropyl-1,3-diaminopropane, dodecyloxyethoxyethylamine, dodecyloxypropyl-1,3-diaminopropane, isotridecyloxypropyl-1,3-diaminopropane and tetradecyloxypropyl-1,3-diaminopropane. More preferred is n-decylthioethylamine.

In the present composition the amount of Formula (I) ranges from about 1 through about 95% by weight, preferably from about 2 through about 40% by weight, more preferably from about 5 through about 25% by weight.

Another characteristic of the compounds of Formula (I) that makes this composition especially advantageous is that they penetrate into the various fouling masses without the use of any penetration aides. For example it is a common practice to use, to concurrently add or to formulate together surfactants and/or dispersants along with biocides or biostats to achieve multifunctional properties such as those provided by the compounds of Formula (I). Most other active ingredients that are not compounds of Formula (I) and used in such industrial systems require such penetration aides to be effective to remove or disperse deposits as they are designed and used for bulk water or planktonic uses.

Hydrophilic polymer, HP, is another required component of the composition and provides a hydrophilic matrix that allows slow diffusion of water into the tablet. Thus the HP allows water to diffuse into the tablet and swell the matrix and thereby allowing the compounds of Formula (I) to diffuse out of the tablet. The HP does not actually need to dissolve to allow this diffusion to happen. While not wishing to be bound by theory, it is believed that when the tablet contacts water, the portion of the tablet that is nearest the perimeter begins to swell due to water absorption. As a result, the active components of the composition in that zone become more mobile and diffuse from the tablet into the surrounding water system. At the same time the viscous outer layer impedes diffusion of water into the interior of the tablet. As time progresses, water permeates further into the tablet and continues to facilitate the gradual release of the components of the present composition. If the HP is actually water soluble, the outer portions of the tablet will also begin to slowly dissolve upon extended contact with water and continue until the entire tablet dissolves. The rate of swelling and/or dissolution of HP are dependent on its structure and its molecular weight. Thus the release rate of components of the composition may be designed by the choice of HP and its molecular weight.

This HP may also be highly water-swellable but not water soluble. This feature may result from a low degree of crosslinking. The tablet will still release the components of the composition but the swollen HP will remain undissolved.

It is important to note that no water is added to the present composition after the tablet is formed and no additional heating is performed, i.e., no added curing process is needed or adjustment of the water content; only when the tablet is placed into contact with water in the industrial water system is any further water in contact with the tablet, which causes the desired slow release as described above.

Examples of suitable HPs are: HPMC, MC, HPC, HEC, CMC, other cellulosic polymers, PEG, starch derivatives, guar derivatives, xanthan gum, carrageenan, gelatin, PVP, and mixtures thereof. High molecular weight polymers are preferred. For example, molecular weights of water soluble polymers are conveniently expressed in terms of their solution viscosities in water at 20° C. and 2 wt % concentration. Thus, HPMC having a solution viscosity of 10,000 to 100,000 mPa·s is preferred, especially from 50,000 to 80,000 mPa·s. The concentration of the HP in the composition ranges from about 5 through about 99% by weight, preferably from about 20 through about 40% by weight, more preferably from about 30 through about 35% by weight.

A compression agent is an optional component that is not used when the composition is other than a tablet or other solid form. The liquid DTEA II® requires this solid compression agent to overcome the negative properties from DTEA II® for the mechanical handling and processing to make the tablet. When DTEA II® is present in greater than about 5% by weight in the tablet, the compression agent is required to be used to stiffen the soft composition and is present from about 1 through about 70% by weight. Examples of suitable compression agents are: DCP, $CaSO_4$, MCC, and lactose. This compression agent is used in the composition in amounts from 0 through about 70% by weight, preferably from about 8 through about 50% by weight, more preferably from about 12 through about 45% by weight. It is only zero when a form of composition other than a tablet is desired or when there is less than about 5% of the compounds of Formula (I) in the tablet.

In contrast to some tablets described in the prior art that are produced by compression of solid active ingredients alone, the present composition provides for a solid tablet from a liquid active ingredient [i.e. compound of Formula (I)] with the aid of a solid HP and optional compression agent.

When the following additional properties are desired, the following further components are present:

A scale inhibitor is added to the composition such as acrylate and maleate copolymers of low to medium molecular weight, [e.g. $M_w$=500-50,000 g/mol], organophosphonates [e.g., HEDP], or other scale inhibitors or mixtures thereof. The above composition may also contain polyacrylate as the preferred scale inhibitor.

The scale inhibitor is used in the composition in a range from 0 through about 50% by weight, preferably from about 10 through about 40% by weight, more preferably from about 20 through about 30% by weight.

A corrosion inhibitor is added to the composition such as $ZnCl_2$, HEDP, DCP and other known agents. The corrosion inhibitor is used in the composition in a range from 0 through about 20% by weight, preferably from about 2 through about 20% by weight, more preferably from about 12 through about 20% by weight. Note that DCP has some corrosion inhibition properties in addition to its use as a compression agent, its primary purpose. Thus its concentration in the composition of this invention will only be accounted for as a compression agent.

Usual other components may be present but are not required, such as antifoam agents [e.g., Dow Corning™ Antifoam H-10 Emulsion, Dow Corning™ 2-42485, Dow Corning™ 1920, Tergitol™ L-62 (The Dow Chemical Company), Hi-Mar DFC-455 (Hi-Mar Specialty Chemicals LLC), Hi-Mar DFC-21, Hi-Mar N-206 HS] from about 0.5 to about 10% by wt or mold release agents (e.g., calcium stearate, stearic acid, polyethyleneglycol, and silicones) from about 0.5 to about 10% by wt. Water may be added to the components as an aid in granulation of the solid components with the liquid compound of Formula (I), where the granules are then dried and pressed into tablets. If some water remains in the tablet after it's pressed, it is less than 10% by weight and usually 5% by weight or less. No further water is added to the tablet and no further drying of the tablet is required.

When all of these properties are present in one solid composition, then it is termed DTEA II® SR SC, or DTEA II® SR Plus, or DTEA II® SR Plus SC.

A preferred composition of this invention is a solid form, especially a tablet. If the tablet composition is not made according to this invention, then the resulting tablet will not have practical mechanical strength and does not release the active components in a desired manner.

These compositions do not require solid chemical feeder systems to dissolve the solid formulation or strong spray of water or some form of ablative liquid stream to dissolve the solid tablet.

The making of these solid tablets is not a simple matter as they must possess substantial mechanical strength for processing and handling. The tablets may be brittle and crumble or soft and flow unless they are carefully made using the above specified amounts of each component. Thus it is not a simple matter to construct these tablets in one uniform, mixed form without any polymer coating and have them remain intact for use.

The specific properties of the compound of Formula (I) enable multiple end uses of the composition. Selection of the desired component of Formula (I), HP and other desired components to make this composition enable this composition to be tuned for the specific conditions of a specific industrial water system site. Surprisingly, the various components also appear to have synergistic behavior compared to their properties when used individually. While not wishing to be bound by theory, it is believed that the ionic DTEA II® may be interacting with other ionic components in the tablet and the resulting complex may slow the diffusion of DTEA II® from the tablet. Because of these enhanced properties, lesser amounts are required to attain the prior effect from each component. This is a cost advantage and has environmental improvements. Additionally, tablets of different composition of this invention can be useful to achieve enhanced (faster or slower) release rates of the active ingredients. This is a surprising advantage of this new composition.

The present composition provides a method to treat industrial water systems with a simple solid composition of this invention for a variety of needs by adjusting the components in the tablet. This solid composition can provide biodispersant, antimicrobial (i.e., bactericide, fungicide, and algaecide), inorganic scale inhibition (hard water), surface bound (sessile) organic deposit inhibition, organic deposit control, microbe-induced corrosion inhibition and other corrosion properties. The tablet can be specifically designed for the particular customers needs while still making the use simple for those treating the water at the industrial water system. The tablet should dissolve slowly so that re-treatment can be scheduled and is not daily, thereby reducing labor costs and errors as well as the time and effort needed to apply the treatment to the industrial waste system. For this invention, the term "slow release" means that compositions of this invention display a slow release in which the active ingredients are fully released into the water system over from about 1 day to about 6 months, preferably from about 1 to about 16 weeks, and more preferably from about 1 to about 4 weeks.

Another advantage of the composition of this invention is the elimination of the use of liquid chemical pumps and chemical piping or chemical lines that are costly and require maintenance and installation. In turn this eliminates the hazard of toxic chemical liquid handling and the need to dispose of chemical waste such as the chemical containers. This reduces the hazards of over-exposure of these chemicals to personnel or the environment.

Because of the slow release property of the tablet of the present composition, it can be effective at much lower doses of the active components than available in the liquid form. Because of the fact that the compound of Formula (I) is gradually released in low concentrations over time, the present solid maintains a minimum effective concentration level and minimizes losses due to absorption, decomposition and purge of the water volume from the system.

In one aspect, the utilities provided by this composition, included in one composition, are as a biocide, biostat, biodispersant, deposit penetrant aid, organic deposit remover, detergent, surfactant, scale inhibitor, scale remover and corrosion inhibitor, which provide sustained release or continuous release of the ingredients over time. This combination has a slow release rate of the active components into water and provides enhanced properties, including synergism, over a longer release time, of all components. Thus the various components have enhanced functionality that is greater than the individual components.

It was unexpected to find a slow release composition of this invention that works under one or all of these conditions (such as high alkaline pH and high water hardness) for a long time and controls fouling, including inorganic, organic, microbial and corrosion.

The invention will be further clarified by a consideration of the following examples, which are intended to be purely exemplary of the present invention.

EXAMPLES

Example 1

Tablet Production

Solid compositions of this invention, preferably tablets, were made from the above discussed components by mixing them, adding water if needed, drying the mixture, granulating the mixture, and then pressing into tablets. The tablet dimensions were 4, 6 or 9 cm in diameter and 1.8-2.3 cm thick, ranging in weight from 24 to 118 g.

Example 2

Tablet Compositions Prepared

Recirculation rate of 1300 L/min (78 m$^3$/h)
Holding capacity of 1000 L
Makeup of 90 L/h
Blowdown of 30 L/h
Evaporation+drift of 60 L/h
Cycle of 3
Running time of 10 h/day, 5 days/week Tablets of the present composition of the invention were placed in the top distribution tray in the cooling tower as follows:

Test 1:

3 tablets of Samples from Example 2 were tested at one time, 50 g/tablet, 6 cm×1.8 cm for:

Weight of tablet loss after 3 weeks: Sample 1=75%; Sample 3=80%; Sample 4=60%. Sample 1 provided the best mechanical and physical properties and dissolved at a desirable rate; and Effectiveness: low corrosion rate and effective bacterial growth control were demonstrated. Corrosion rate=0.55 mil/yr carbon steel; 0.23 mil/yr copper; microbial growth=plate count=$10^3$ cfu/mL, initial plate count=$10^5$ cfu/mL.

Test 2:

4 tablets of Sample 6 from Example 2 were used, 60 g/tablet, 6 cm×2.3 cm for effectiveness: low corrosion rate and effective bacterial growth control: corrosion rate=5.2 mil/yr carbon steel; 0.34 mil/yr copper; microbial growth=plate count=$10^3$ cfu/mL, initial plate count=$10^6$ cfu/mL.

Example 4

Tablet Testing—Cooling Towers

Tablet Sample 8 (60 g) from Example 2 was tested in four different industrial water systems as shown in the following table, demonstrating its effectiveness for corrosion, scale, and

| Component | Agent | 1 | 2 | 3 | 4 | 5 | 6 | 7 | 8 |
|---|---|---|---|---|---|---|---|---|---|
| Compound of Formula (I) | DTEA II ® | 20 | 13 | 25 | 20 | 35 | 15 | 10 | 8 |
| HP | HPMC | 33 | 28 | 33 | 33 | 33 | 30 | 32 | 35 |
| HP | PEG | 0 | 0 | 0 | 0 | 0 | 0 | 4 | 5 |
| Compression Agent | DCP | 42 | 54 | 37 | 0 | 0 | 30 | 18 | 16 |
| Compression Agent | MCC | 0 | 0 | 0 | 42 | 27 | 0 | 0 | 0 |
| Scale Inhibitor | Poly-acrylate | 0 | 0 | 0 | 0 | 0 | 15 | 15 | 15 |
| Scale & corrosion Inhibitor | HEDP | 0 | 0 | 0 | 0 | 0 | 5 | 8 | 15 |
| Corrosion Inhibitor | ZnCl$_2$ | 0 | 0 | 0 | 0 | 0 | 0 | 7 | 0 |
| Antifoam | Dow Corning 2-42485 | 0 | 0 | 0 | 0 | 0 | 0 | 4 | 0 |
| Antifoam | Dow Corning 1920 | 0 | 0 | 0 | 0 | 0 | 0 | 0 | 2 |
| Water* | | 5 | 5 | 5 | 5 | 5 | 5 | 2 | 4 |
| Total | | 100 | 100 | 100 | 100 | 100 | 100 | 100 | 100 |

For the compositions prepared as Samples 1-8 above, the numbers in the table are % by weight.
*is the amount of water used to prepare the granules and not the amount in the final tablet.

Example 3

Tablet Testing—Cooling Tower

In a commercial cooling tower having the following characteristics:

microbial control. Results vary depending on the particular operating conditions, which may be more challenging, such as use of reclaimed water or 12 hour/day operating times. Microbial control was demonstrated by average total bacterial counts of $10^3$, as compared to typical counts of $10^5$-$10^6$ for untreated systems.

| | System # | | | | |
|---|---|---|---|---|---|
| | 1 | 2 | 3 | 4 (treated) | 4 (untreated) |
| Volume/Size | 100 RT | 300 RT | 120 RT | 60 RT | 60 RT |
| Type of Industrial Water System | Process | Air Conditioning | Process | Air Conditioning | Air Conditioning |

-continued

| | System # | | | | |
|---|---|---|---|---|---|
| | 1 | 2 | 3 | 4 (treated) | 4 (untreated) |
| Water Source | Tap Water | Tap Water | Reclaimed Water | Tap Water | Tap Water |
| # Cycles | 4.2 | 4.8 | Not recorded | 3.4 | 3.7 |
| Operation Hours/Day | 24 | 24 | 24 | 12 | 12 |
| Total Trial Time (days) | 100 | 74 | 49 | 80 | 80 |
| Dosage/Month (60-g tablets) | 5 | 15 | 8 | 2 | 0 |
| Circulating water pH | 8.9 | 8.97 | Not recorded | 8.83 | 8.78 |
| Conductivity (µS/cm) | 1228 | 1373 | Not recorded | 1410 | 1428 |
| Total Organic Phosphate (ppm) | 0.3 | 1.95 | Not recorded | 0.5 | 0.12 |
| Total Phosphate (ppm) | 0.45 | 2.21 | Not recorded | 0.9 | 0.2 |
| Average total bacterial counts (cfu/mL) | $10^3$ | $10^3$-$10^4$ | $10^3$ | $10^3$ | Not recorded |
| Carbon Steel Corrosion Rate (mpy) | 0.75 | 1.43 | 5.37 | 6.08 | Not recorded |
| Admiralty Brass Corrosion Rate (mpy) | 0.19 | 0.08 | 0.34 | 0.28 | Not recorded |
| Scaling Index Deviation %* | 13 | −5 | not available | 15 | 42 |

*Scaling Index Deviation % = [(make up Ca—H × Cycles) − (actual Ca—H)/(make up Ca—H × Cycles)] × 100;
note:
Ca—H means calcium hardness value.
Lower scaling index deviations indicate better scaling control.

Example 5

Tablet Testing—Recirculated Water Tank

Figure 2:
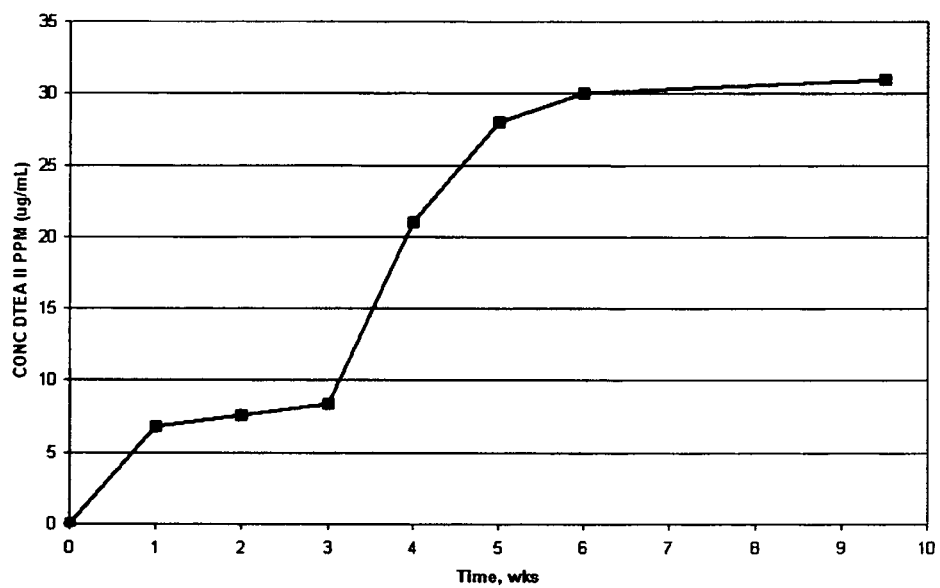
FIG. 2 shows DTEA II® concentration vs. time for Example 2, Sample 6 and its slow release over 9.5 weeks.
Figure 3:
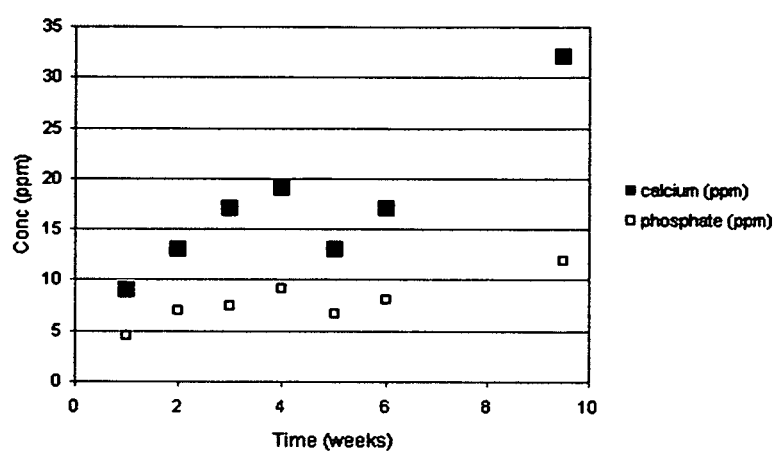
FIG. 3 shows the release of calcium and phosphate ion over 9.5 weeks from Sample 6 in Example 2.

One tablet in a mesh bag was suspended in 30 gal of water with slow water recirculation. Water was sampled and tablets were visually observed weekly. Two tablet compositions were separately tested from Example 2, Samples 1 and 6. Water was analyzed for DTEA II®, phosphate, and calcium concentrations vs. time. FIGS. 1-3 show the results obtained. FIG. 1 shows that DTEA II® in Sample 1 was released slowly from the tablet over the course of 9 weeks. FIG. 2 shows that DTEA II® in Sample 6 was also released slowly from the tablet over the course of 9 weeks but at a slower rate than for Sample 1. These results show that the composition of the tablet can affect the DTEA release rate in an unexpected way. FIG. 3 shows that Ca and $PO_4$ ions for Sample 6 were also released slowly over 9 weeks. Clearly, the present composition allows activity for at least 9 weeks and releases the components in a slow release manner.

Example 6

Tablet Testing—Cooling Tower Deposit Removal

Figure 4:
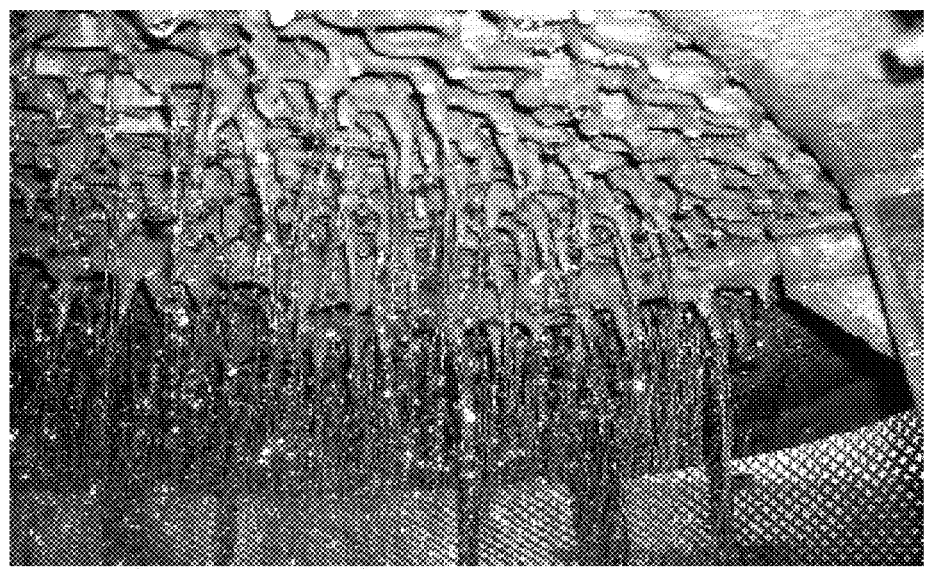
FIG. 4 is a copy of a photograph showing surfaces having fouling in a cooling tower prior to treatment by Sample 8 in Example 2.
Figure 5:
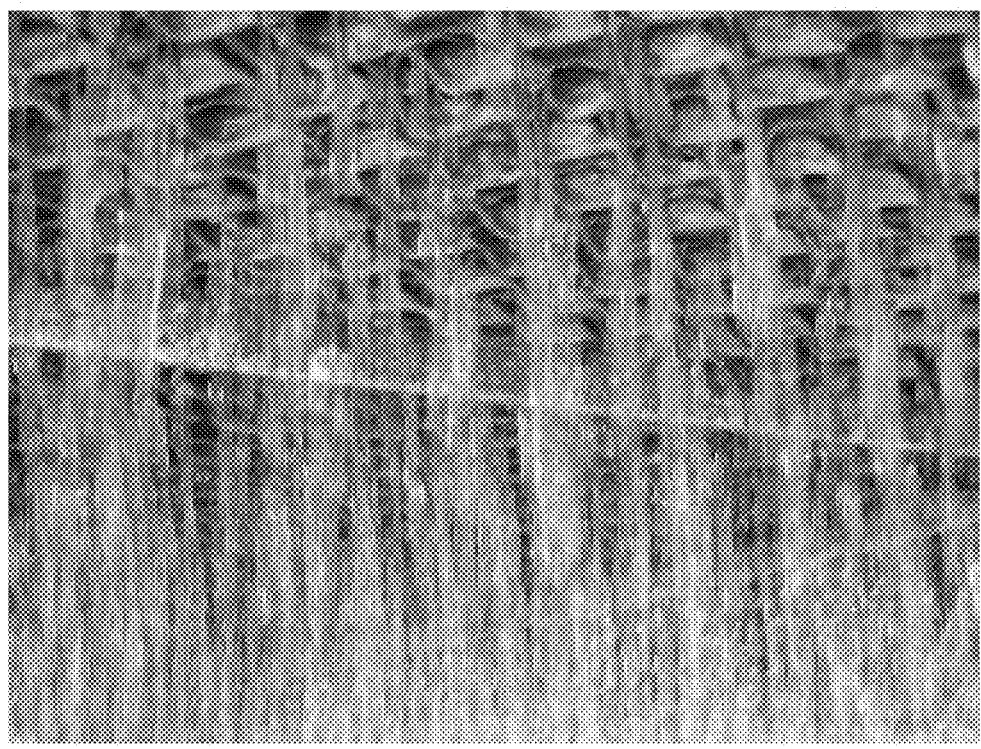
FIG. 5 is a copy of a photograph showing surfaces having reduced fouling in a cooling tower 5 weeks after treatment by Sample 8 in Example 2.

FIGS. 4 and 5 are before and after photographs which illustrate the effectiveness of treatment of an air conditioning cooling water system by Sample 8 of Example 2. Note the deposit removal after 5 weeks.

Example 7

Tablet Testing—Recirculated Water Tank

Figure 6:
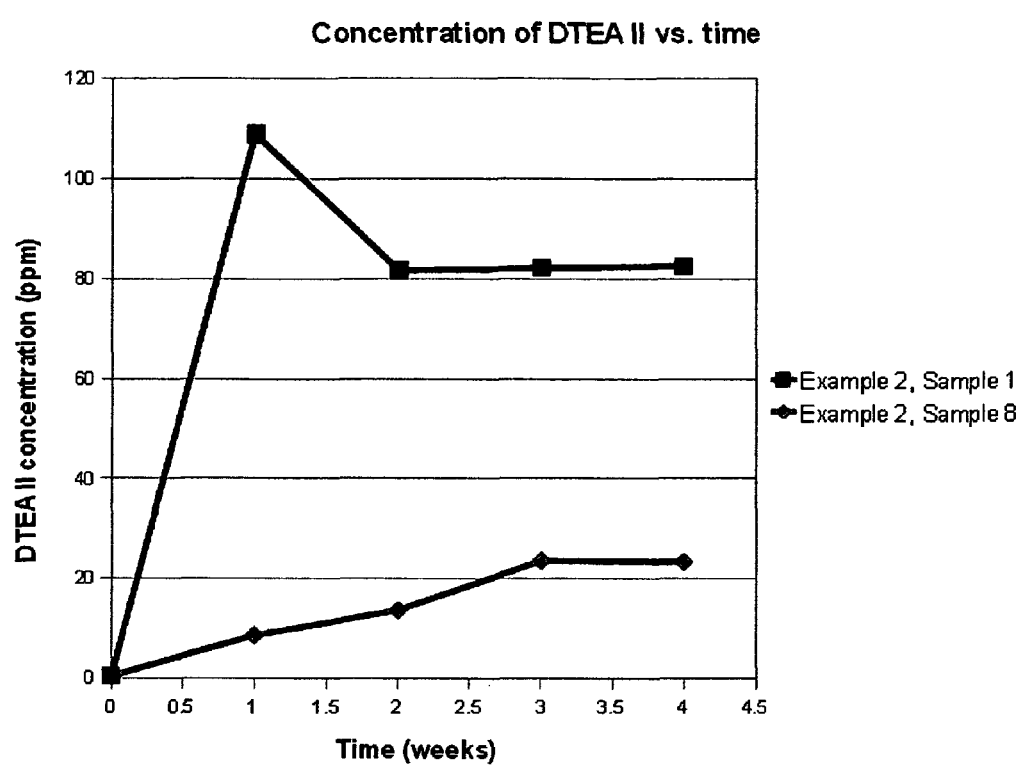
FIG. 6 shows DTEA II™ concentration vs. time for Example 2, Samples 1 and 8 and its slow release over 4 weeks.

Two 33-g tablets of Example 2, Sample 1 were stacked on top of each other, held together in a mesh bag, and suspended in 30 gal of water with moderate water recirculation. The water was circulated and heated to 85-90° F. for 8 hours/day, 5 days/week. Heating and circulation were stopped during the overnight hours. Water was sampled and tablets were visually observed weekly. Similarly, in a separate tank, three 33-g tablets of Example 2, Sample 8 were stacked and held in a mesh bag in the water flow. Water analysis for DTEA II® concentration vs. time is shown in FIG. 6. Note that DTEA II® in Sample 1 is released at a faster rate than in Sample 8. Visual observation of the two tablets at three weeks showed that Sample 1 was almost entirely dissolved while Sample 2 was still 2.7 inches in diameter. These results show that the composition of the tablet can affect the DTEA II® release rate in an unexpected way.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter.

What is claimed is:
1. A slow release solid tablet composition for industrial water systems which comprises:
   a) from about 2 through about 40% by weight of an amphiphilic, liquid compound of Formula (I)

$$R—X—R^1—NH_2$$

wherein:
   R is a straight chain or branched chain $C_6$-$C_{18}$ alkyl or a straight chain or branched chain $C_6$-$C_{18}$ alkyloxy-$C_2$-$C_3$-alkyl;
   $R^1$ is a straight chain or branched chain $C_2$-$C_4$ alkyl; and
   X is S, O or N—$R^2$ wherein $R^2$ is H or a straight chain or branched chain $C_1$-$C_8$ alkyl; or
   organic or inorganic acid addition salts thereof; and
   b) from about 20 through about 40% by weight of a hydrophilic polymer selected from hydroxypropyl methylcellulose (HPMC), methyl cellulose (MC), hydroxypropylcellulose (HPC), hydroxyethylcellulose (HEC), and polyethylene glycol (PEG), or mixtures of them; and
   c) from about 8 through about 50% by weight of an ionic compression agent selected from dicalcium phosphate (DCP) and $CaSO_4$; and
   d) from 0 through about 50% by weight of a scale inhibitor selected from polyacrylate, acrylate copolymers and maleate copolymers wherein the polymers are of low to medium molecular weight, [e.g. $M_w$=500-50,000 g/mol], and organophosphonates [e.g., 1-hydroxyethylidene-1,1-diphosphonate (HEDP)]; or other scale inhibitors or mixtures thereof; and
   e) from 0 through about 20% by weight of a corrosion inhibitor selected from $ZnCl_2$, and 1-hydroxyethylidene-1,1-diphosphonate (HEDP) or other known agents; and f) that the total of the components of a)-e), plus when present any other typical tablet components, equal 100% by weight of the tablet composition; and provided that the following occur when in use:
  i) it is used in a water circulation system under operation conditions of multiple cycles while maintaining activity; and
  ii) it removes, disperses, or inhibits biofilm deposits; and/or
  iii) it removes, disperses, or inhibits organic deposits; and
  iv) the slow release of the active components of the composition in such industrial water system is complete in from about 1 day to about 6 months.

2. The composition of claim 1 wherein in the compound of Formula (I) R is a straight chain or branched chain $C_6$-$C_{18}$ alkyl.

3. The composition of claim 2 wherein R is a straight chain or branched chain $C_8$-$C_{14}$ alkyl.

4. The composition of claim 1 wherein in the compound of Formula (I) X is N—$R^2$ where $R^2$ is H.

5. The composition of claim 1 or 3 wherein in the compound of Formula (I) X is S or O.

6. The composition of claim 5 wherein the compound of Formula (I) is n-decylthioethylamine.

7. The composition of claim 1 wherein the hydrophilic polymer is hydroxypropyl methylcellulose (HPMC) having an aqueous viscosity of 50,000 to 80,000 mPa·s at a 2 wt % concentration at 20° C.

8. The composition of claim 1 wherein the compound of Formula (I) is present in greater than 5% by weight in the tablet.

9. The composition of claim 1 wherein the scale inhibitor is present from 10 through 40% by weight.

10. The composition of claim 1 wherein the corrosion inhibitor is present from 2 through 20% by weight.

11. The composition of claim 1 wherein other typical tablet components are also present such as an antifoam agent.

12. The composition of claim 1 wherein the water to be treated is cycled from 2 through 5 cycles.

13. The composition of claim 1 wherein the water to be treated has high water hardness, about from 70 ppm to ≥2,000 ppm.

14. The composition of claim 1 wherein the water to be treated has an alkaline pH from about 7.1 to about 12.

15. The composition of claim 1 wherein the slow release of the active components is from about 1 to about 16 weeks.

16. A method of using a composition of claim 1 as an anti-fouling agent by placing the composition into the water of an industrial water system.

17. The composition of claim 1 wherein from about 10 through about 40% by weight of a scale inhibitor and from about 2 through about 20% by weight of a corrosion inhibitor are present.

18. A method of using a slow release solid tablet composition of claim 1 or 17 in industrial water systems by placing the composition into the water of the system wherein the composition
  a) is used under operation conditions of multiple cycles while the composition maintains activity; and
  b) removes, disperses, or inhibits biofilm deposits; and/or
  c) removes, disperses, or inhibits organic deposits; and
  d) provides a slow release of the active components of the composition in such industrial water system which is complete in from about 1 day to about 6 months.

19. The method of claim 18 wherein the water to be treated has high water hardness, about from 70 ppm to ≥2,000 ppm.

20. The method of claim 18 wherein the water to be treated has an alkaline pH from about 7.1 to about 12.

21. The method of claim 18 wherein the industrial water system is operated at from 2 through 5 cycles.

* * * * *